United States Patent
Choi et al.

(10) Patent No.: US 10,179,132 B2
(45) Date of Patent: Jan. 15, 2019

(54) COMPOSITION FOR INDUCING DIFFERENTIATION OF MULTIPOTENT NEURAL STEM CELLS INTO DOPAMINERGIC NEURONS AND METHOD FOR INDUCING DIFFERENTIATION OF MULTIPOTENT NEURAL STEM CELLS INTO DOPAMINERGIC NEURONS BY USING THE SAME

(71) Applicant: INDUSTRY-ACADEMIC COOPERATION FOUNDATION, YONSEI UNIVERSITY, Seoul (KR)

(72) Inventors: Kang-Yell Choi, Seoul (KR); Mi-Yeon Kim, Incheon (KR); Yeong-Mun Kim, Seoul (KR)

(73) Assignee: INDUSTRY-ACADEMIC COOPERATION FOUNDATION, YONSEI UNIVERSITY, Seoul (KR)

(*) Notice: Subject to any disclaimer, the term of this patent is extended or adjusted under 35 U.S.C. 154(b) by 0 days.

(21) Appl. No.: 15/455,954

(22) Filed: Mar. 10, 2017

(65) Prior Publication Data
US 2017/0209451 A1    Jul. 27, 2017

Related U.S. Application Data

(63) Continuation-in-part of application No. 14/877,527, filed on Oct. 7, 2015, now abandoned.

(30) Foreign Application Priority Data

May 26, 2015   (KR) .................. 10-2015-0073016

(51) Int. Cl.
*A61K 31/44*   (2006.01)
*A61K 31/519*  (2006.01)
(Continued)

(52) U.S. Cl.
CPC .......... *A61K 31/519* (2013.01); *A61K 31/166* (2013.01); *A61K 31/18* (2013.01);
(Continued)

(58) Field of Classification Search
CPC ............ A61K 31/4418; A61K 31/4412; A61K 31/519; A61K 31/166; A61K 31/4184
(Continued)

(56) References Cited

U.S. PATENT DOCUMENTS

2009/0093462 A1    4/2009  Abel et al.
2016/0177260 A1*   6/2016  Shoji .................... C12N 5/0619
                                                  424/93.21

FOREIGN PATENT DOCUMENTS

KR    1005192270000     9/2005
WO    WO2013/093137   *  6/2013
(Continued)

OTHER PUBLICATIONS

WO 2013/093137 English Translation.*
(Continued)

*Primary Examiner* — Shengjun Wang
(74) *Attorney, Agent, or Firm* — Duane Morris LLP; Gregory M. Lefkowitz; Jason M. Nolan

(57) ABSTRACT

Disclosed is a composition for inducing the differentiation of neural stem cells into dopaminergic neurons. The composition includes the compound represented by Formula 1 ("AS703026") as a MEK 1/2 inhibitor. Also disclosed is a method for inducing the differentiation of neural stem cells into dopaminergic neurons by using the composition. Dopaminergic neurons whose differentiation from neural stem cells is induced by the composition and method can be applied to cell replacement therapies and gene therapies for the treatment of neurodegenerative diseases, such as Parkinson's disease, or can be widely used as materials for the
(Continued)

examination of drug effects or numerous studies in the development of new drugs.

6 Claims, 10 Drawing Sheets

(51) Int. Cl.
    *A61K 31/277*     (2006.01)
    *A61K 31/166*     (2006.01)
    *A61K 31/4184*     (2006.01)
    *A61K 31/4412*     (2006.01)
    *A61K 31/18*     (2006.01)
    *A61K 35/30*     (2015.01)
    *C07D 213/81*     (2006.01)
    *C12N 5/0793*     (2010.01)

(52) U.S. Cl.
    CPC ........ *A61K 31/277* (2013.01); *A61K 31/4184* (2013.01); *A61K 31/44* (2013.01); *A61K 31/4412* (2013.01); *A61K 35/30* (2013.01); *C07D 213/81* (2013.01); *C12N 5/0619* (2013.01); *C12N 2501/727* (2013.01)

(58) Field of Classification Search
    USPC ..................... 514/352, 350, 264.1, 387, 615
    See application file for complete search history.

(56) References Cited

FOREIGN PATENT DOCUMENTS

| WO | 2013178320 | 12/2013 |
|---|---|---|
| WO | 2015020234 | 2/2015 |

OTHER PUBLICATIONS

Martinelli, et al., "Antitumor activity of pimasertib, a selective MEK 1/2 inhibitor, in combination with PI3K/mTOR inhibitors or with multi-targeted kinase inhibitors in pimasertiv-resistant human lung and colorectal cancer cells", Int. J. Cancer; 133, pp. 2089-2101 (2013).

* cited by examiner

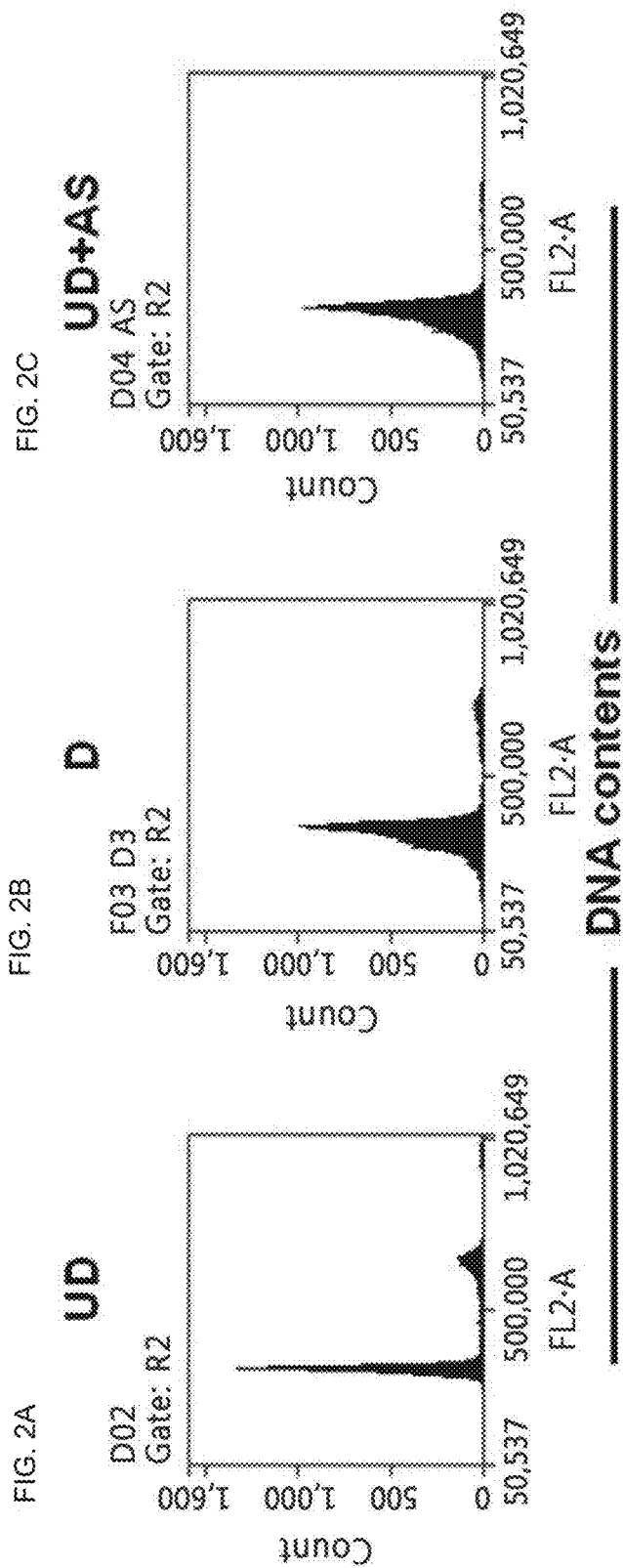

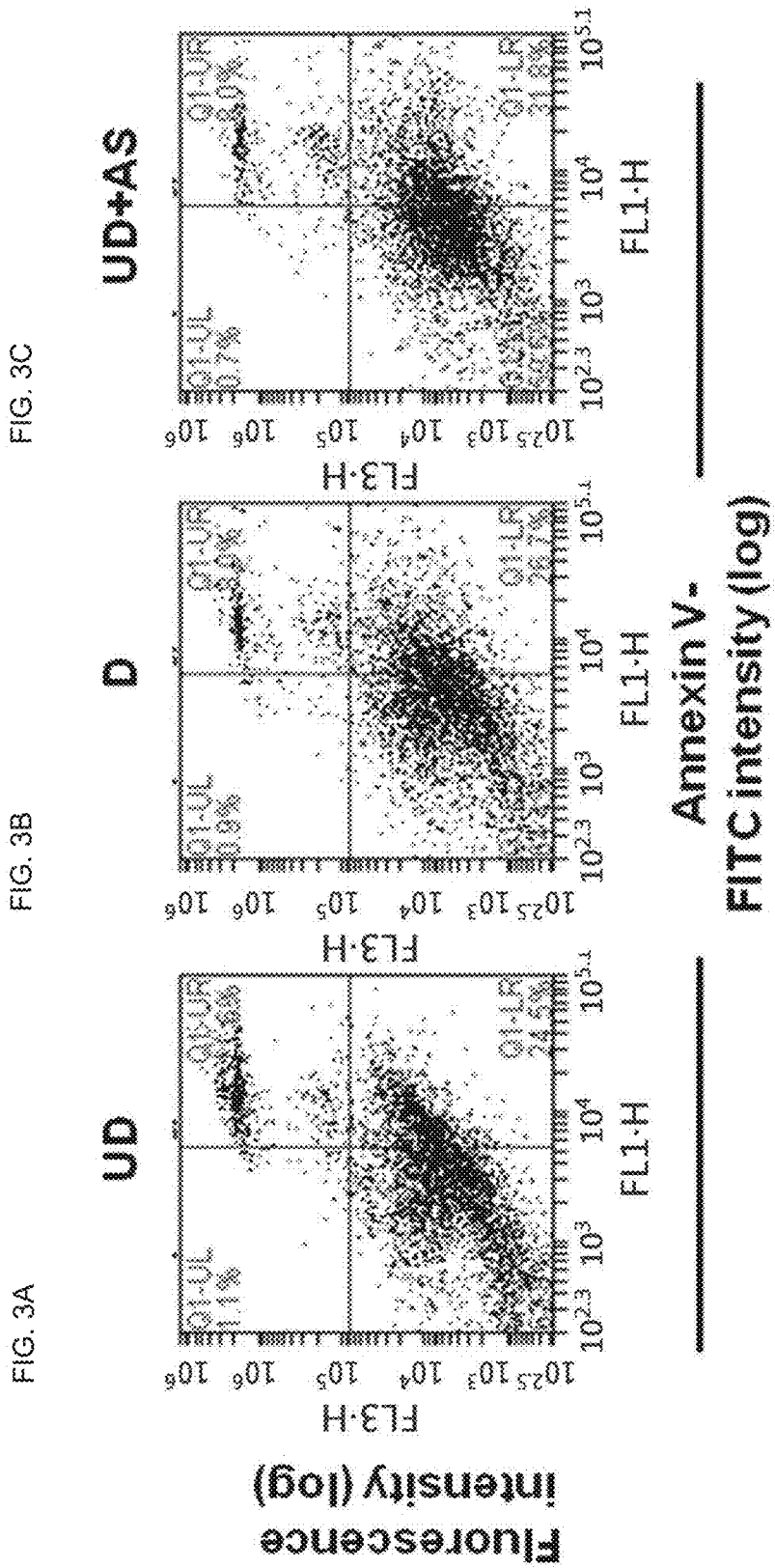

COMPOSITION FOR INDUCING DIFFERENTIATION OF MULTIPOTENT NEURAL STEM CELLS INTO DOPAMINERGIC NEURONS AND METHOD FOR INDUCING DIFFERENTIATION OF MULTIPOTENT NEURAL STEM CELLS INTO DOPAMINERGIC NEURONS BY USING THE SAME

CROSS-REFERENCE TO RELATED APPLICATIONS

This application is a continuation-in-part of U.S. application Ser. No. 14/877,527, filed Oct. 7, 2015, which claims priority under 35 U.S.C. § 119 to Korean Patent Application No. 10-2015-0073016 filed on May 26, 2015, the disclosures of which are incorporated herein by reference in its entirety.

BACKGROUND OF THE INVENTION

1. Field of the Invention

The present invention relates to a composition for inducing the differentiation of neural stem cells into dopaminergic neurons. More specifically, the present invention relates to a composition capable of specifically inducing the differentiation of neural stem cells into dopaminergic neurons without apoptosis while preventing differentiation into other brain cells, and a method for inducing the differentiation of neural stem cells into dopaminergic neurons by using the composition.

2. Description of the Related Art

Parkinson's disease is the most common neurodegenerative disease but senile dementia and the majority of patients with the disease are elderly. With increasing aging population, the number of patients with Parkinson's disease increases exponentially. Thus, much attention is focused on developing therapies for stopping the progress of Parkinson's disease or recovering damaged brain tissues.

Although the exact cause of Parkinson's disease is not yet established, it is known that Parkinson's disease is caused by destruction of dopamine-secreting dopaminergic neurons in the substantia nigra of the brain. The lack of dopamine leads to damage to the motor pathways of the brain, causing various symptoms of Parkinson's disease.

Research has been conducted on the treatment of Parkinson's disease in various fields. Some potential approaches to the treatment of Parkinson's disease have been proposed, for example, drug therapies using several mimetics and artificial neuron stimulation methods by surgery, such as deep-brain stimulation. However, drug therapies have side effects caused by short-term chronic administration, making it difficult to treat Parkinson's disease. Surgical therapies impose heavy physical and economic burdens on patients and their therapeutic effects other than temporary alleviation of symptoms are difficult to expect. Thus, there is an absolute need for alternative therapies for Parkinson's disease.

Gene therapy and cell transplantation are known as therapeutic methods that can be used to replace lost neurons in neurodegenerative diseases. Once damaged, brain nerve tissues have very limited capacity of self-regeneration. For this reason, there are currently no effective therapies for these diseases.

PRIOR ART DOCUMENTS

Patent Documents

Korean Patent No. 10-0519227

SUMMARY OF THE INVENTION

The present invention is intended to provide a composition capable of specifically inducing the differentiation of neural stem cells into dopaminergic neurons and a method for differentiating neural stem cells into dopaminergic neurons by using the composition.

One representative aspect of the present invention is directed to a composition for inducing the differentiation of neural stem cells into dopaminergic neurons, including a MEK 1/2 inhibitor.

The MEK 1/2 inhibitor may be selected from the compounds represented by Formulae 1 to 10:

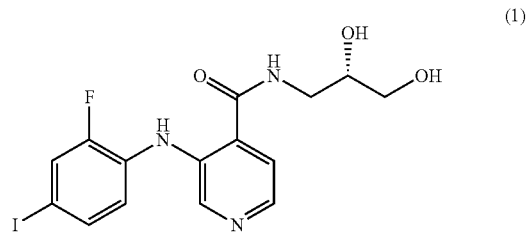 [SMILES: O=C(NC[C@H](O)CO)c1ccncc1Nc1ccc(I)cc1F]

(1)

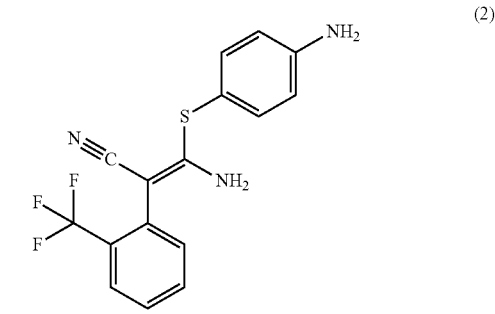

(2)

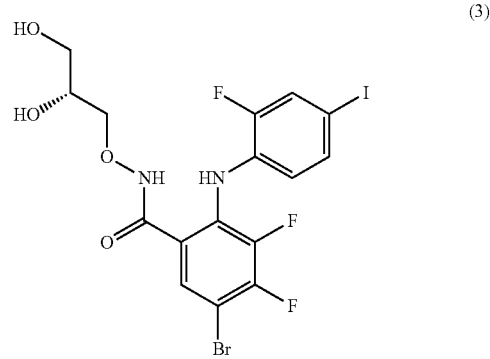

(3)

(4)
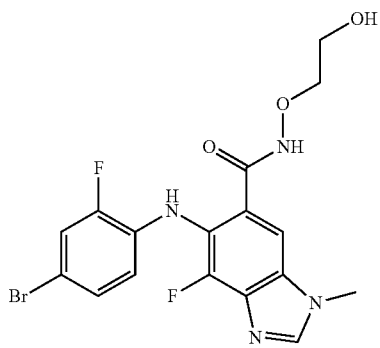

(5)
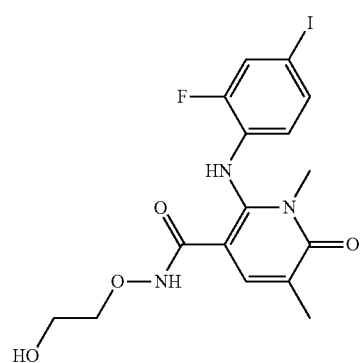

(6)
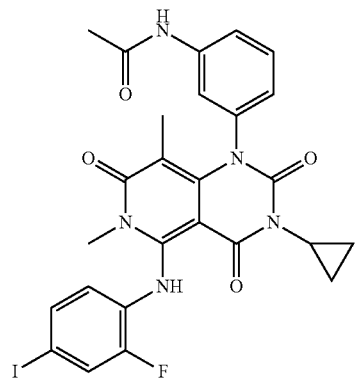

(7)
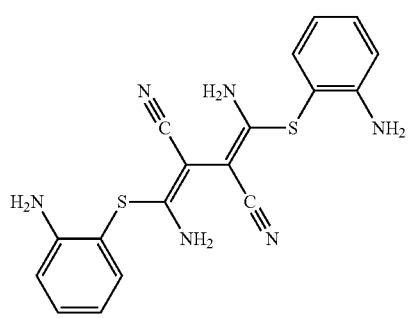

(8)
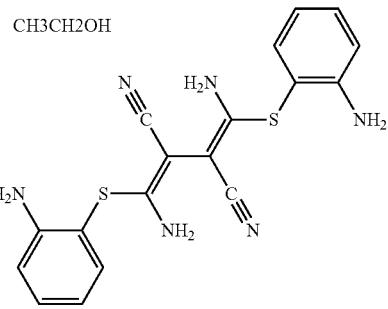

(9)
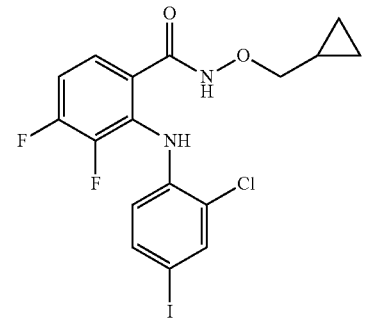

(10)
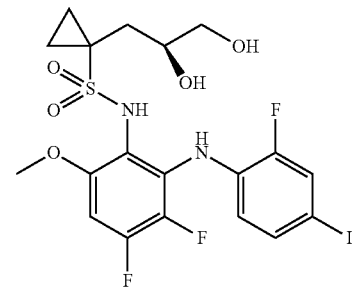

The MEK 1/2 inhibitor may be the compound represented by Formula 1:

(1)
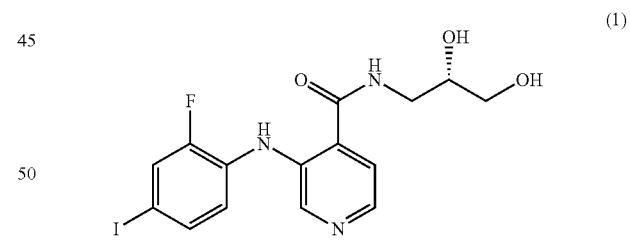

The MEK 1/2 inhibitor may be present at a concentration of 0.1 to 20 μM.

The MEK 1/2 inhibitor may be present at a concentration of 1 to 10 μM.

The use of the composition is accompanied by inhibition of growth of cancer cells from neural stem cells.

A further representative aspect of the present invention is directed to a method for inducing the differentiation of neural stem cells into dopaminergic neurons by using a composition for differentiation induction including a MEK 1/2 inhibitor.

The MEK 1/2 inhibitor may be selected from the compounds represented by Formulae 1 to 10:

(1)
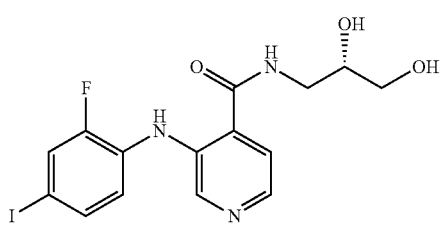
(2)
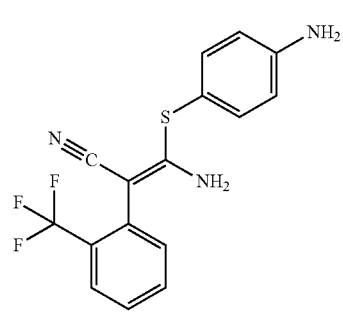
(3)
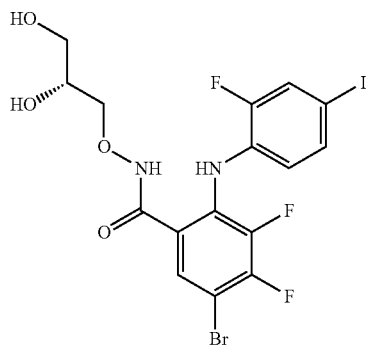
(4)
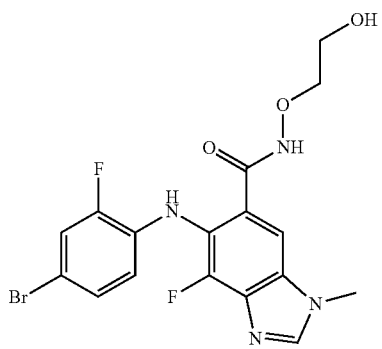
(5)
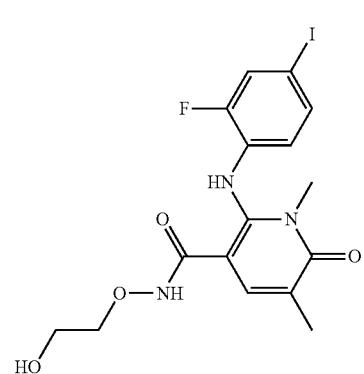
(6)
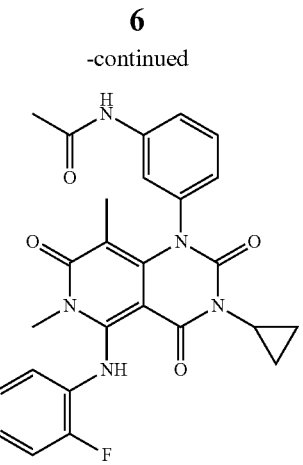
(7)
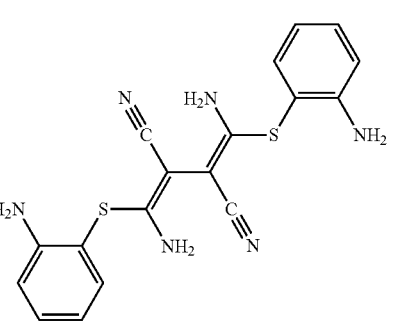
CH3CH2OH
(8)
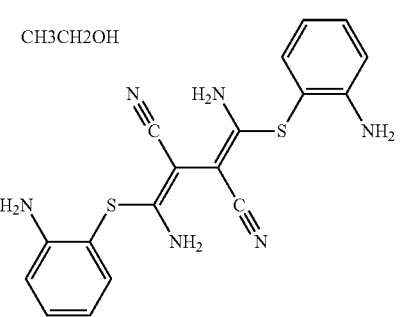
(9)
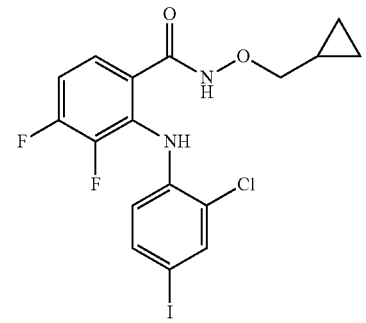
(10)
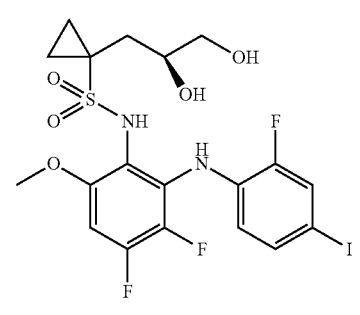

The MEK 1/2 inhibitor may be the compound represented by Formula 1:

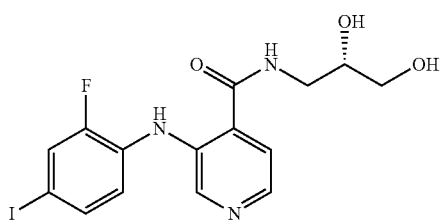

The method includes inoculating neural stem cells into the composition for differentiation induction including the MEK 1/2 inhibitor and allowing the neural stem cells to differentiate for 1 to 7 days until completion.

Another representative aspect of the present invention is directed to a pharmaceutical composition for the prophylaxis or treatment of Parkinson's disease, including the composition for differentiation induction and neural stem cells as active ingredients.

The composition and the method for differentiation induction according to the present invention can effectively induce the differentiation of neural stem cells into dopaminergic neurons due to the use of the MEK 1/2 inhibitor selected from various compounds. Dopaminergic neurons differentiated from neural stem cells by the present invention can be applied to cell replacement therapies and gene therapies for the treatment of neurodegenerative diseases, such as Parkinson's disease, or can be widely used as materials for the examination of drug effects or numerous studies in the development of new drugs.

BRIEF DESCRIPTION OF THE DRAWINGS

These and/or other aspects and advantages of the invention will become apparent and more readily appreciated from the following description of the embodiments, taken in conjunction with the accompanying drawings of which:

FIG. 2A is a histogram which shows the result of flow cytometry for neural progenitor PI stained cells (undifferentiated; UD) cultured in Example 1;

FIG. 2B is a histogram which shows the result of flow cytometry for differentiated PI stained cells (D) cultured in Comparative Example 1;

FIG. 2C is a histogram which shows the result of flow cytometry for AS703026-treated PI stained cells (UD+AS) cultured in Example 2 to identify the cycles of the cells;

FIG. 3A is a scatter plot diagram which shows the result of flow cytometry for neural progenitor annexin-V/PI stained cells (undifferentiated; UD) cultured in Example 1;

FIG. 3B is a scatter plot diagram which shows the result of flow cytometry for differentiated annexin-V/PI stained cells (D) cultured in Comparative Example 1;

FIG. 3C is a scatter plot diagram which shows the result of flow cytometry for AS703026-treated annexin-V/PI stained cells (UD+AS) cultured in Example 2 to identify the cycles of the cells;

DETAILED DESCRIPTION OF THE INVENTION

Figure 1A:
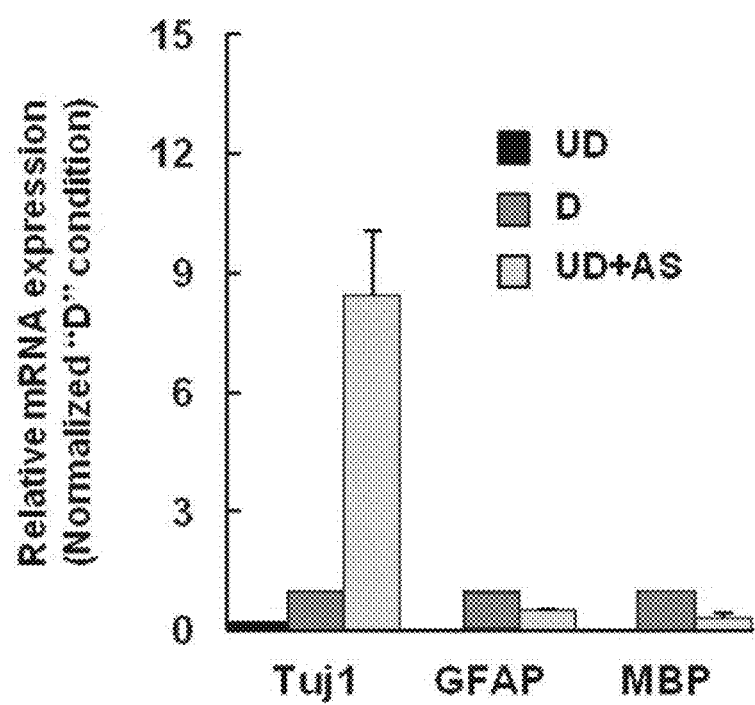
FIG. 1A shows the expression level of Tuj1, a neuronal differentiation factor, in the AS703026-treated cells (UD+AS) cultured in Example 2 was a maximum of at least 10 times higher than those in the neural progenitor cells (undifferentiated; UD) cultured in Example 1 and the differentiated cells (D) cultured in Comparative Example 1.

Several aspects and various embodiments of the present invention will now be described in more detail.

As used herein, the term "differentiation" refers to a phenomenon in which the structure or function of cells is specialized during division, proliferation, and growth of the cells.

According to one aspect of the present invention, there is disclosed a composition for inducing the differentiation of neural stem cells into dopaminergic neurons which includes a MEK 1/2 inhibitor.

As used herein, the term "MEK 1/2 inhibitor" refers to a substance that simultaneously targets MEK 1 and MEK 2 as upstream molecules of ERK 1/2 during mitogen-activated protein kinase/extracellular regulated kinase (MEK/ERK) signaling.

Unlike the MEK 1/2 inhibitor used in the present invention, a substance (e.g., PD98059 (MEK 1 inhibitor)) targeting either MEK 1 or MEK 2 fails to induce the differentiation of neural stem cells into dopaminergic neurons or causes cytotoxicity, resulting in apoptosis of neural stem cells before differentiation into dopaminergic neurons.

For example, MEK1 inhibitor PD98059 does not induce substantial differentiation of neural stem cells into dopaminergic neurons due to its inability to inhibit MEK 2.

Specifically, the MEK 1/2 inhibitor may be selected from the compounds represented by Formulae 1 to 10:

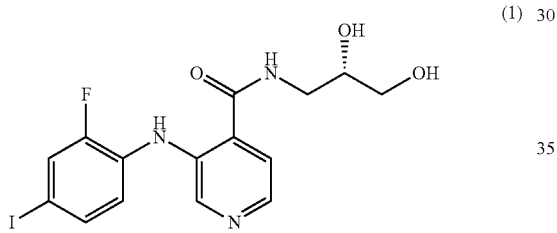

(1)

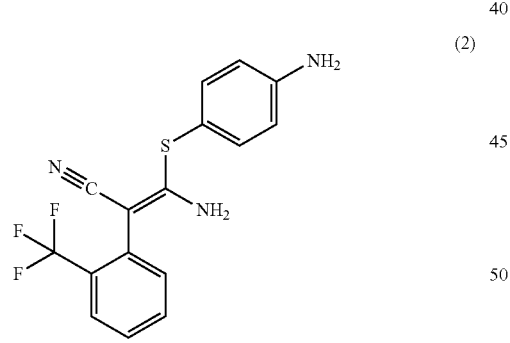

(2)

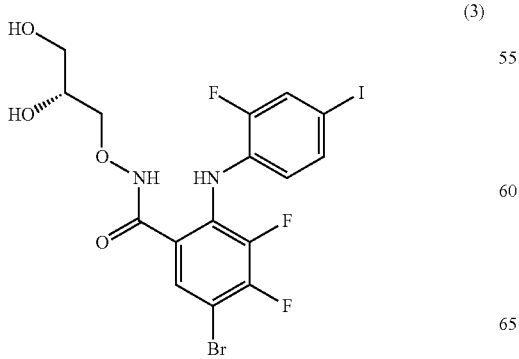

(3)

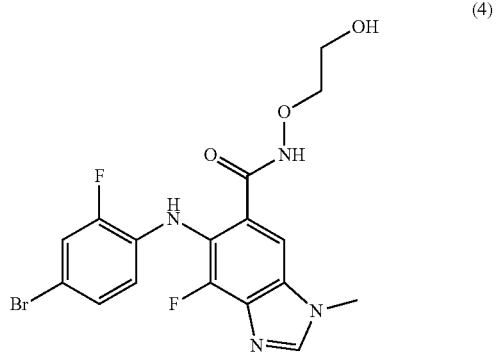

(4)

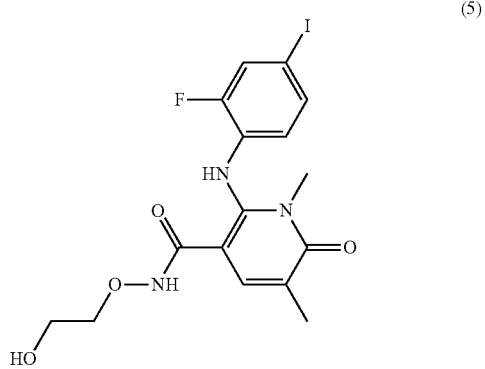

(5)

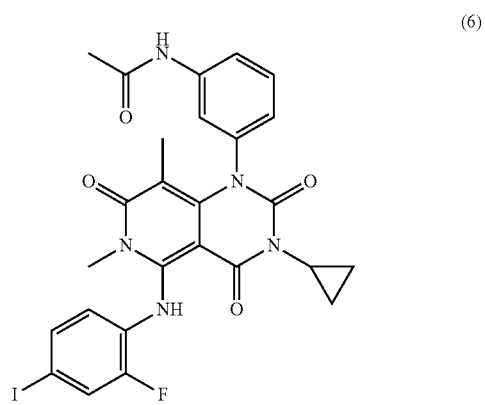

(6)

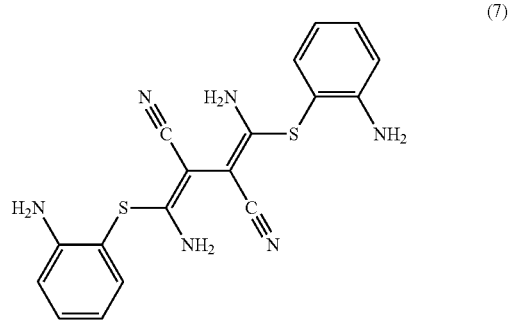

(7)

-continued

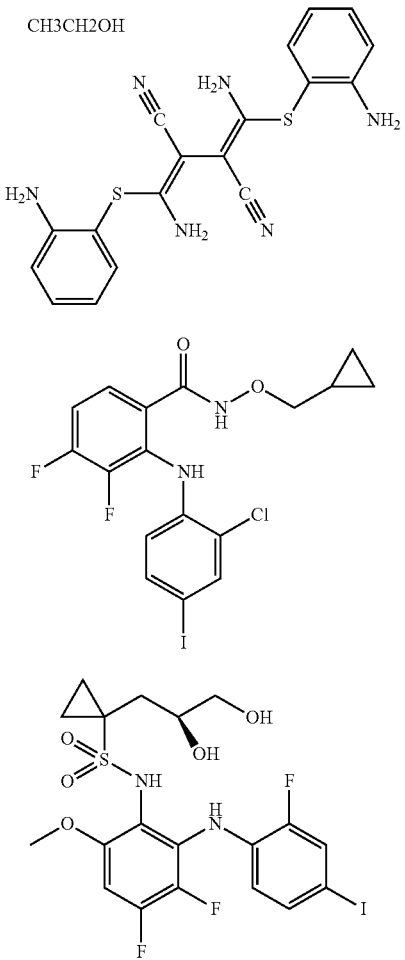

More specifically, the MEK 1/2 inhibitor may be the compound represented by Formula 1:

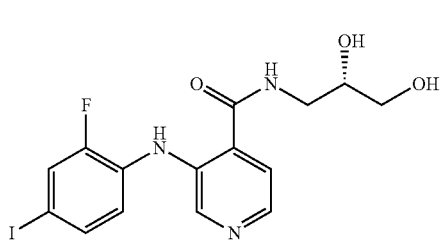

The compound represented by Formula 1 is a low molecular weight compound that has the chemical name N-[(2S)-2,3-dihydroxypropyl]-3-[(2-fluoro-4-iodophenyl)amino] isonicotinamide hydrochloride.

As described in the following experimental examples section, the compound represented by Formula 1 as the MEK 1/2 inhibitor used in the present invention more effectively induces the differentiation of neural stem cells into dopaminergic neurons than other MEK 1/2 inhibitors and does not cause apoptosis of neural stem cells before differentiation into dopaminergic neurons because it has no cytotoxicity. That is, the use of the compound represented by Formula 1 leads to differentiation into a large amount of dopaminergic neurons. Particularly, the compound represented by Formula 1 has an IC50 value of 5 to 10 nM, which is significantly low compared to the IC50 values of the compounds represented by Formulae 2 to 10. Due to this low IC50 value, the compound represented by Formula 1 behaves as an ATP non-competitive allosteric inhibitor with low cytotoxicity, and as a result, it efficiently induces specific differentiation of neural stem cells into dopaminergic neurons rather than into other types of cells.

To the best of our knowledge, little is known about the use of MEK 1/2 inhibitors for inducing the differentiation of neural stem cells into dopaminergic neurons and the specific role of MEK 1/2 inhibitors in the differentiation of neural stem cells.

Particularly, the compound represented by Formula 1 has the least cytotoxicity and is most effective in inducing specific differentiation of neural stem cells into dopaminergic neurons rather than other cells. As described above, the composition for differentiation induction including the compound represented by Formula 1 effectively inhibits both MEK 1 and MEK 2 activities through ATP-non competitive allosteric binding, demonstrating that the compound represented by Formula 1 induces specific differentiation of neural stem cells into dopaminergic neurons without causing cytotoxicity and apoptosis.

In the Examples section that follows, particularly the compound represented by Formula 1 was confirmed to induce the differentiation of neural stem cells isolated from mouse embryos (E10.5) into dopaminergic neurons, inhibit differentiation into other cells, and suppress growth of cancer cells from neural stem cells.

Neural stem cells whose differentiation into dopaminergic neurons is induced by the composition including the compound represented by Formula 1 are undifferentiated cells that can be differentiated into neurons. The neural stem cells are cells in the early stage of differentiation of neurons that can differentiate into dopaminergic neurons, astrocytes, and oligodendrocytes. The neural stem cells may be those derived from animals.

The animals are intended to include livestock, such as cattle, pigs, sheep, horses, dogs, mice, rats, and cats, as well as humans and primates. The animals are preferably humans.

The composition for differentiation induction may further contain a medium component known to those skilled in the art, in addition to the MEK 1/2 inhibitor.

Specifically, any suitable component for serum-free media may be used without limitation in the composition for differentiation induction. The use of Dulbecco's Modified Eagle's Medium/Nutrient Mixture (DMEM/F12) (1:1) is preferred.

The composition for differentiation induction may further contain one or more medium components selected from the group consisting of 90-110 μM putrescine, 20-40 nM selenite, 10-30 nM progesterone, 1.0-2.0 mg/ml d-(+)-glucose, 20-30 μg/ml insulin, 0.05-0.2 μg/ml apo-transferrin, 0.3-0.6 mM alanyl glutamine, 50-150 IU/ml penicillin, and 50-150 μg/ml streptomycin.

In the Examples section that follows, the present inventors have attempted to find an optimum composition for differentiating neural stem cells from animals into dopaminergic neurons, and as a result, found that the composition of the present invention specifically induces the differentiation of neural stem cells isolated from grown mouse embryos into dopaminergic neurons.

The present inventors have also found that the expression levels of TH and Tuj1 as markers of dopaminergic neurons are about 10-fold lower and those of other markers of brain cells are higher when neural stem cells are differentiated using conventional compositions for differentiation induction than using the composition of the present invention, indicating that the conventional compositions induces the differentiation of a larger amount of the neural stem cells into cells other than dopaminergic neurons.

The MEK 1/2 inhibitor, particularly the compound represented by Formula 1, used in the composition of the present invention behaves as an ATP non-competitive allosteric inhibitor that inhibits both MEK 1 and MEK 2 in neural stem cells to promote specific differentiation into dopaminergic neurons without cytotoxicity and does not induce differentiation into other types of cells. This selective induction of differentiation enables the production of a large number of dopaminergic neurons despite the use of the compound represented by Formula 1 at a low concentration. Due to this advantage, the composition for differentiation induction including the compound represented by Formula 1 is very suitable for use in the development and production of therapeutic agents for neurodegenerative diseases, such as Parkinson's disease.

The compound of Formula 1 used in the composition of the present invention is a MEK 1/2 inhibitor that has been tested as a drug to treat cancer patients in a phase II clinical trial but has not yet been used to treat nervous system diseases.

In conclusion, the presence of the MEK 1/2 inhibitor in the composition of the present invention is effective in inducing specific differentiation of neural stem cells into dopaminergic neurons. The present invention has been achieved based on these findings.

The composition for differentiation induction including the MEK 1/2 inhibitor, particularly the compound represented by Formula 1, inhibits the MEK/ERK signaling system in neural stem cells and induces specific differentiation into dopaminergic neurons. Particularly, the composition of the present invention induces the differentiation of neural stem cells into dopaminergic neurons without apoptosis but does not induce differentiation into other brain cells, such as astrocytes and oligodendrocytes. Accordingly, when the composition of the present invention is used for a therapeutic purpose, the incidence of side effects encountered in conventional treatments using neural stem cell cultures can be reduced.

That is, since the composition of the present invention is involved in the EGFR→Ras→Raf-1→MEK→ERK pathway to induce differentiation into dopaminergic neurons by proliferation inhibition, it can induce specific differentiation into desired dopaminergic neurons without causing growth of cancer cells. Therefore, the composition of the present invention is very useful in the production of therapeutic dopaminergic neurons.

Figure 6:
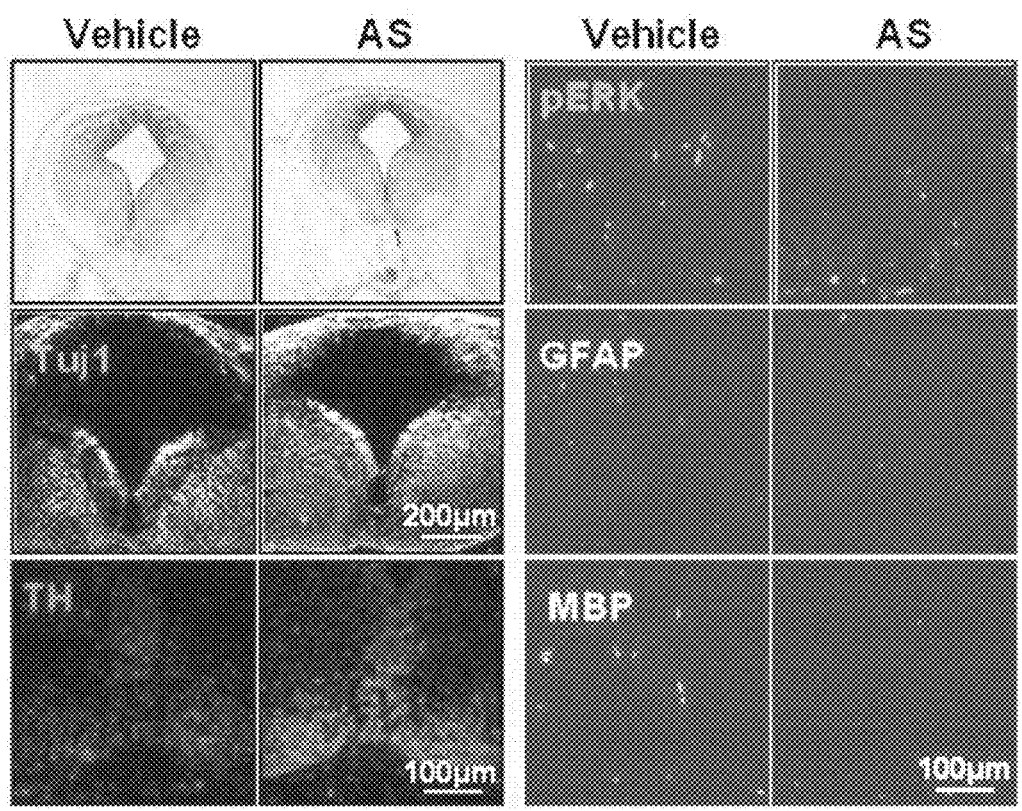
FIG. 6 shows the results of immunocytochemical analysis using neuronal markers on the expression levels of the markers in the ventral midbrains, where dopaminergic neurons are most abundantly distributed, collected from the embryos of pregnant mouse models at 10.5 days of gestation for 4 days sacrificed after a composition for differentiation induction including AS703026 was administered intraperitoneally to the mouse models and the embryos of pregnant mouse models at 10.5 days of gestation for 4 days sacrificed after the composition was not administered intraperitoneally to the mouse models in order to observe the therapeutic effects of the composition on the dopaminergic neurons.
Figure 7:
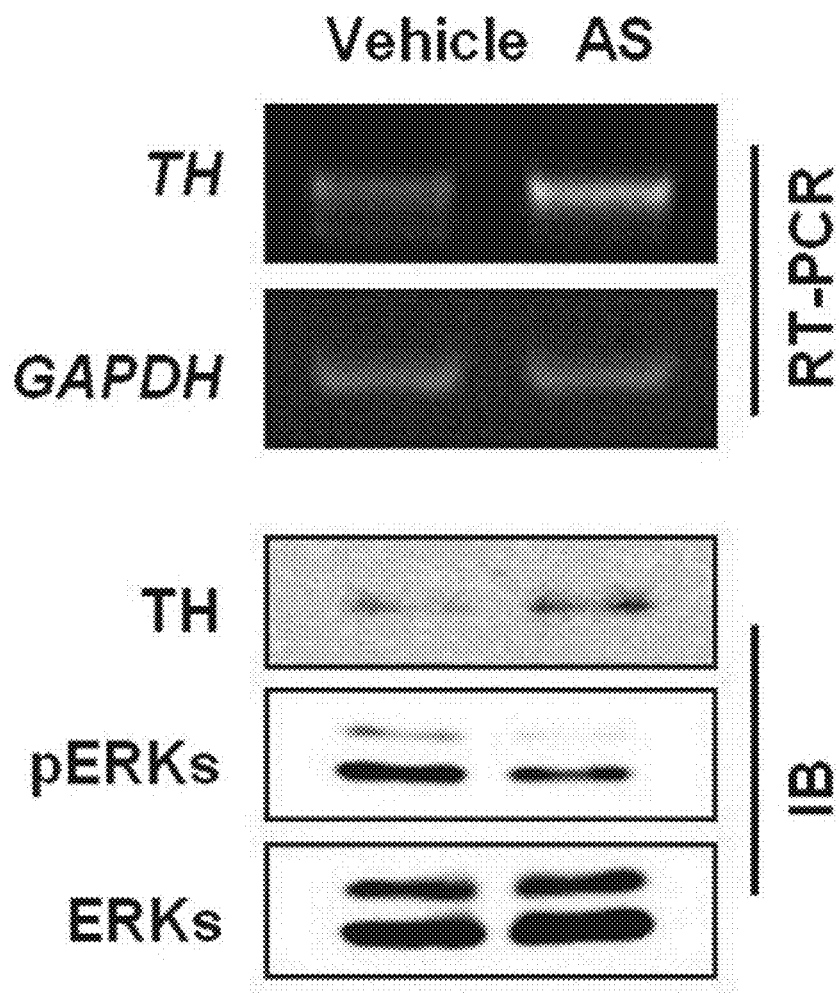
FIG. 7 shows the results of RT-PCR analysis for the expression levels of markers in the ventral midbrains, where dopaminergic neurons are most abundantly distributed, collected from the embryos of pregnant mouse models at 10.5 days of gestation for 4 days sacrificed after the composition for differentiation induction including AS703026 was administered intraperitoneally to the mouse models and the embryos of pregnant mouse models at 10.5 days of gestation for 4 days sacrificed after the composition was not administered intraperitoneally to the mouse models in order to observe the therapeutic effects of the composition on dopaminergic neurons.

In the Examples section that follows, the present inventors have attempted to confirm whether the composition for differentiation induction can induce differentiation into dopaminergic neurons in in vivo experiments, and as a result, found that when the composition is administered intraperitoneally to pregnant mouse models, the concentrations of dopaminergic neurons in the brains of the animal embryos increase and are at least 2-fold lower than those in the brains of the embryos of non-administered pregnant mouse models (see FIGS. 6 and 7).

According to a further aspect of the present invention, there is disclosed a method for inducing the differentiation of neural stem cells into dopaminergic neurons by using a composition for differentiation induction including a MEK 1/2 inhibitor.

The present inventors have made an effort to develop a method for inducing the differentiation of neural stem cells into dopaminergic neurons, and as a result, found that when neural stem cells are treated with a composition for differentiation induction including a MEK 1/2 inhibitor, particularly the compound represented by Formula 1, the composition induces specific differentiation of the neural stem cells into dopaminergic neurons while preventing differentiation into other brain cells, demonstrating that the use of the composition is effective in producing dopaminergic neurons.

There is no particular restriction as to the source of the neural stem cells. For example, the neural stem cells may be isolated from embryonic stem cells by any suitable method known in the art. Alternatively, the neural stem cells may be purchased from the market or may be cultured by any suitable method known in the art. In the Examples section that follows, neural stem cells isolated from the frontal lobes of day 14.5 mouse embryos were used.

Before differentiation, the neural stem cells may be inoculated into a culture medium and cultured at 35 to 40° C. The culture medium may be any serum-free medium including a growth factor but is preferably Dulbecco's Modified Eagle's Medium/Nutrient Mixture (DMEM/F12) (1:1) including a growth factor.

The composition for differentiation induction may further contain one or more medium components selected from the group consisting of 90-110 μM putrescine, 20-40 nM selenite, 10-30 nM progesterone, 1.0-2.0 mg/ml d-(+)-glucose, 20-30 μg/ml insulin, 0.05-0.2 μg/ml apo-transferrin, 0.3-0.6 mM alanyl glutamine, 50-150 IU/ml penicillin, and 50-150 μg/ml streptomycin.

The growth factor may be selected from the group consisting of 10-30 ng/ml bFGF, 10-30 ng/ml EGF, and mixtures thereof.

Before differentiation, the neural stem cells may be cultured in Dulbecco's modified Eagle's medium (DMEM)/F12 (1:1) supplemented with 100 μM putrescine, 30 nM selenite, 20 nM progesterone, 1.55 mg/ml d-(+)-glucose, 25 μg/ml insulin, 0.1 μg/ml apo-transferrin, 0.5 mM alanyl glutamine, 100 IU/ml penicillin, and 100 μg/ml streptomycin.

The neural stem cells are undifferentiated cells that can differentiate into neurons. The neural stem cells are cells in the early stage of differentiation of neurons that can differentiate into dopaminergic neurons, astrocytes, and oligodendrocytes. The neural stem cells may be those derived from animals.

The animals are intended to include livestock, such as cattle, pigs, sheep, horses, dogs, mice, rats, and cats, as well as humans and primates. The animals are preferably humans.

For differentiation, the cultured neural stem cells are inoculated into the composition for differentiation induction including a MEK 1/2 inhibitor. The differentiation may be carried out by any suitable method known in the art. There is no particular restriction on the differentiation induction of the neural stem cells. Preferably, the neural stem cells are directly inoculated into the composition for differentiation induction including a MEK 1/2 inhibitor or the composition for differentiation induction is added to the medium containing the cultured neural stem cells, and the differentiation of the neural stem cells is induced at 35 to 40° C.

The procedure for differentiation of the neural stem cells into dopaminergic neurons depends on the culture conditions (e.g., the kinds and contents of the medium components, and the culture period). The culture conditions are not particularly limited. Preferably, the culture temperature is from 35 to 40° C. at which the differentiation of the neural stem cells into dopaminergic neurons can be induced. If the culture temperature is lower than 35° C. or exceeds 40° C., the neural stem cells undergo apoptosis before differentiation into dopaminergic neurons.

It is necessary to ensure a sufficient concentration of the cells or detect whether the cells are normal or abnormal before addition of the composition for differentiation induction including a MEK 1/2 inhibitor. To this end, it is preferred to treat the neural stem cells with the composition for differentiation induction including a MEK 1/2 inhibitor by the above-described method within a culture period of 7 days or less. The culture period of the neural stem cells is more preferably from at least 0.5 to a maximum of 7 days to ensure a sufficient concentration of the cells.

Generally, the neural stem cells tend to differentiate during culture. The multipotency of the neural stem cells is suppressed by artificial treatment with bFGF or EGF in order to maintain their undifferentiated state before addition of the composition for differentiation induction.

If the neural stem cells are cultured for a period exceeding 7 days, some of the neural stem cells whose multipotency is incompletely suppressed are already differentiated into other brain cells and remain as impurities. As a result, dopaminergic neurons cannot be obtained in high yield despite subsequent addition of the composition for differentiation induction.

That is, it is preferred to treat the neural stem cells with the composition for differentiation induction including the compound represented by Formula 1 within a culture period of 7 days or less.

The MEK 1/2 inhibitor simultaneously inhibits both MEK 1 and MEK 2 acting on the MEK pathway of the RAS-RAF-MEK-ERK signaling pathway, a representative pathway involved in the proliferation and survival of neural stem cells. Accordingly, the MEK 1/2 inhibitor acting on the cells can induce specific differentiation of the neural stem cells into desired dopaminergic neurons without causing growth of cancer cells from the neural stem cells.

More preferably, the MEK 1/2 inhibitor is selected from the compounds represented by Formulae 1 to 10:

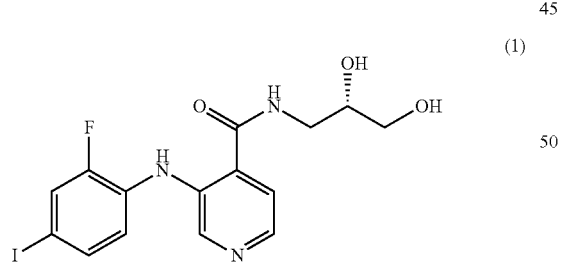

(1)

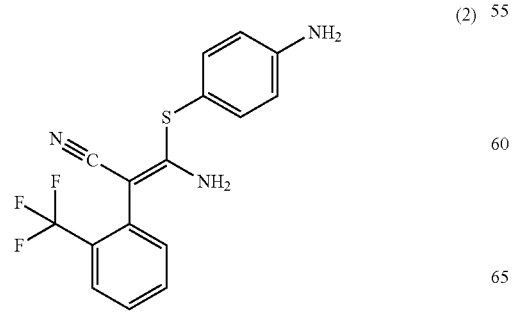

(2)

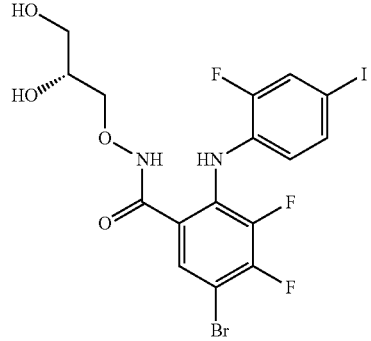

(3)

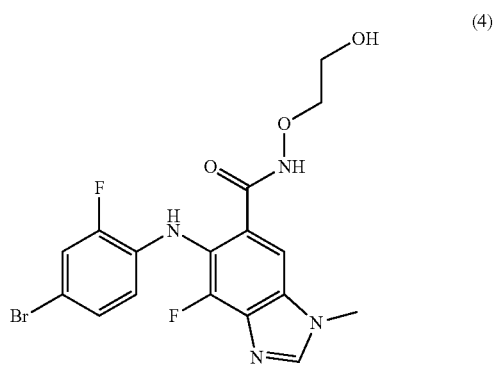

(4)

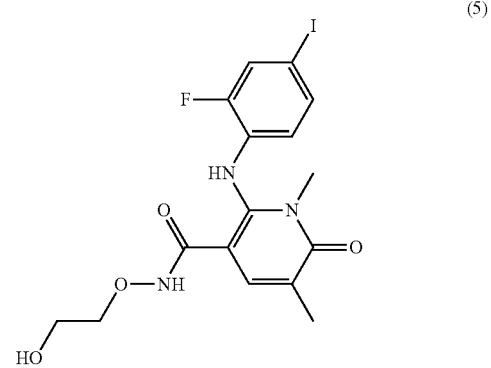

(5)

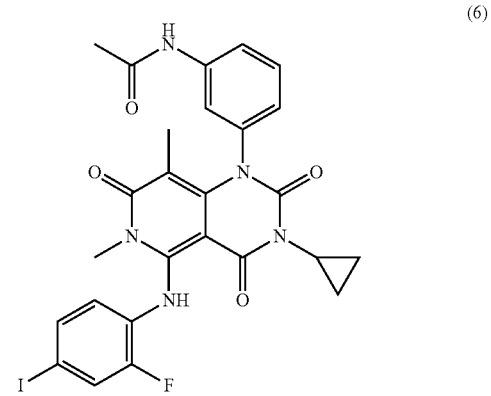

(6)

-continued

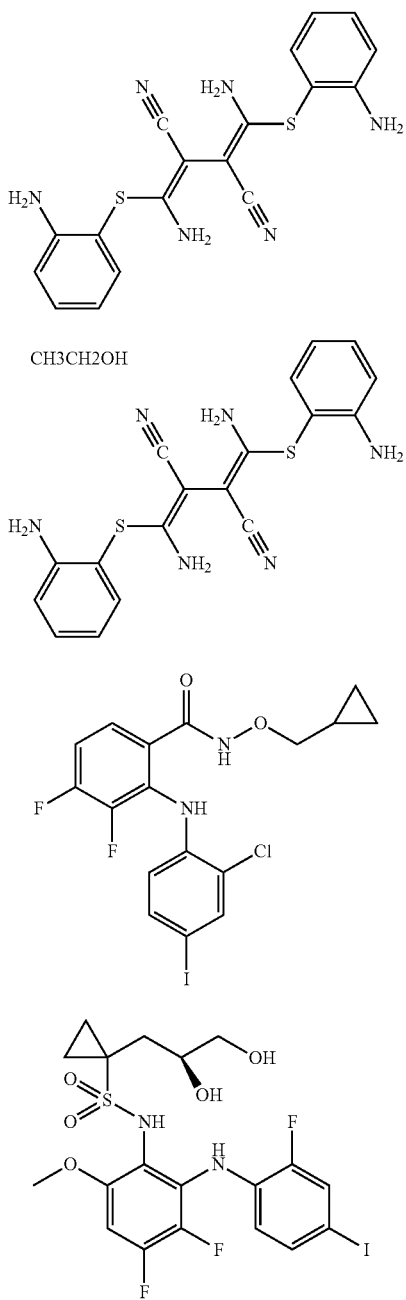

Most preferably, the MEK 1/2 inhibitor is the compound represented by Formula 1:

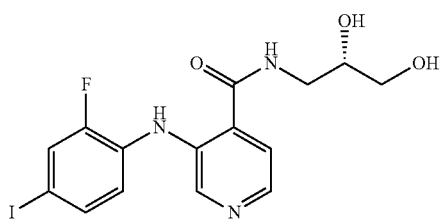

The reason for the choice of the compound represented by Formula 1 is explained by the fact that therapeutic dopaminergic neurons can be produced on a large scale despite the use of a low concentration of the compound.

The compound represented by Formula 1 is a low molecular weight compound that has the chemical name N-[(2S)-2,3-dihydroxypropyl]-3-[(2-fluoro-4-iodophenyl)amino] isonicotinamide hydrochloride.

When it is intended to induce the differentiation of neural stem cells into dopaminergic neurons using the composition for differentiation induction including the MEK 1/2 inhibitor, particularly the compound represented by Formula 1, the concentration of the MEK 1/2 inhibitor is adjusted to 0.1 to 20 µM. The presence of the MEK 1/2 inhibitor at a concentration of less than 0.1 µM does not contribute to an improvement in the ability of the composition to induce the differentiation of neural stem cells into dopaminergic neurons, increasing the possibility that differentiation into other cells may be induced. Meanwhile, the presence of the MEK 1/2 inhibitor at a concentration exceeding 20 µM may cause cytotoxicity.

It is more preferred that the concentration of the MEK 1/2 inhibitor in the composition for differentiation induction is from 1 to 10 µM, which will be described in the following Examples section. If the concentration of the MEK 1/2 inhibitor is less than 1 µM, differentiation into cells other than dopaminergic neurons is not induced but it takes a long time for neural stem cells to differentiate into dopaminergic neurons, which is uneconomical. Meanwhile, if the concentration of the MEK 1/2 inhibitor as an active ingredient exceeds 10 µM, the excess MEK 1/2 inhibitor may extremely inhibit MEK 1/2 affecting many intracellular signaling pathways upon subsequent in vivo administration, and as a result, unwanted reactions may be induced. The inhibitory effect of the MEK 1/2 inhibitor on MEK 1/2 suppresses the formation of cancer cells but may be applied to normal cells.

After addition of the composition for differentiation induction including the MEK 1/2 inhibitor to the medium for the culture of neural stem cells, it takes 1 to 7 days, preferably about 3 to about 5 days, for the differentiation to complete. This enables efficient use of the composition for clinical treatment.

According to the method of the present invention, about 75% of the neural stem cells of a mouse are differentiated into dopaminergic neurons and are larger by about 45 to about 50% than the proportion of the neural stem cells of a mouse differentiated into dopaminergic neurons when the composition for differentiation induction is not added. This indicates that the method of the present invention is excellent in inducing specific differentiation into dopaminergic neurons.

In the Examples section that follows, it was also confirmed that the number of dopaminergic neurons formed in the brains of the sacrificed embryos of pregnant mouse models at 10.5 days of gestation after intraperitoneal administration of the composition for differentiation induction including the MEK 1/2 inhibitor, particularly the compound represented by Formula 1, was approximately twice as large as that in the brains of the sacrificed embryos of non-administered animals. This result indicates that neural stem cells are completely differentiated into dopaminergic neurons by the method of the present invention.

Since the composition of the present invention is involved in the EGFR→Ras→Raf-1→MEK→ERK pathway to induce differentiation into dopaminergic neurons by proliferation inhibition, it can induce specific differentiation into desired dopaminergic neurons without causing growth of cancer cells. Therefore, the composition of the present invention is very useful in the production of therapeutic dopaminergic neurons.

According to another aspect of the present invention, there is disclosed a pharmaceutical composition for the prophylaxis or treatment of a disease associated with dopaminergic neurons, including the composition for differentiation induction and neural stem cells as active ingredients.

The disease associated with dopaminergic neurons is not particularly limited and is intended to include all diseases that are caused by congenital or acquired damage to or loss of dopaminergic neurons. Preferably, the disease is Parkinson's disease.

Before administration of the prophylactic or therapeutic composition including the composition for differentiation induction and neural stem cells as active ingredients to a patient with the disease, ex vivo differentiation of the neural stem cells into dopaminergic neurons is induced and a large number of the dopaminergic neurons proliferate. That is, the patient is administered the dopaminergic neurons, dopaminergic neural progenitor cells during differentiation, and the neural stem cells, and thereafter, the differentiation of the cells is completed under the influence of factors in the body. After differentiation, the dopaminergic neurons are applied to sites where neurons are damaged and lost, achieving therapeutic effects.

Due to the presence of the MEK 1/2 inhibitor, particularly the compound represented by Formula 1, capable of suppressing the growth of cancer cells, the prophylactic or therapeutic composition including neural stem cells can be directly administered to a patient without the need for culture for differentiation.

Since the prophylactic or therapeutic composition has the ability to specifically differentiate dopaminergic neurons, the neural stem cells can be differentiated after inoculation into the composition for differentiation induction and the need for additional purification is not required. Accordingly, the prophylactic or therapeutic composition can be directly administered to a patient without the need for culture for differentiation.

The prophylactic or therapeutic composition of the present invention may further include an immune reaction inhibitor to prevent the incidence of immune rejection response upon implantation.

The prophylactic or therapeutic composition of the present invention can be prepared into general formations known in the art, for example, injectables, and can be directly implanted into the midbrain by surgery.

The dose of the therapeutic composition may vary depending on the condition of the patient, the route, mode, and frequency of administration, the period of treatment, the age and sex of the patient, and the severity of the disease, and can be easily determined by those skilled in the art according to factors known in the medical field.

The prophylactic or therapeutic composition is preferably administered at a dose of 0.5 to 20 mg/day.

The present invention will be explained in more detail with reference to the following examples. However, these examples are not to be construed as limiting or restricting the scope and disclosure of the invention. It is to be understood that based on the teachings of the present invention including the following examples, those skilled in the art can readily practice other embodiments of the present invention whose experimental results are not explicitly presented. Such modifications and variations are intended to come within the scope of the appended claims.

The experimental results of the following examples, including comparative examples, are merely representative and the effects of the exemplary embodiments of the present invention that are not explicitly presented hereinafter can be specifically found in the corresponding sections.

EXAMPLE 1

1) Culture of Mouse Neural Stem Cells

Neural stem cells were isolated from the brain of a day 14.5 mouse embryo, treated with 10 ng/ml human basic fibroblast growth factor (bFGF) (Peprotech, Princeton, N.J.) and 20 ng/ml human epidermal growth factor (EGF) (Peprotech) in a N2 culture medium, and cultured in suspension in a 25 cm$^2$ flask (Nunc, Pittsburgh, Pa.) for 4 days.

Neurospheres were treated with TrypLE and then separated into single cells, which were uniformly seeded into a culture dish coated with 15 μg/ml poly-L-ornithine and 10 μg/ml fibronectin. Following culture, the morphology of the cells was observed.

The N2 culture medium was Dulbecco's modified Eagle's medium (DMEM)/F12 (1:1) supplemented with 100 μM putrescine, 30 nM selenite, 20 nM progesterone, 1.55 mg/ml d-(+)-glucose, 25 μg/ml insulin, 0.1 μg/ml apo-transferrin, 0.5 mM alanyl glutamine, 100 IU/ml penicillin, and 100 μg/ml streptomycin.

EXAMPLE 2

Differentiation into Dopaminergic Neurons

Mouse neural stem cells were cultured in accordance with the procedure of Example 1. To the cultured neural stem cells was added the compound represented by Formula 1 (10 μM, hereinafter also referred to as 'AS703026'), Formula 3 (1 μM, hereinafter also referred to as 'PD318088'), Formula 5 (10 μM, hereinafter also referred to as 'AZD8330'), Formula 6 (1 μM, hereinafter also referred to as 'Trametinib') or Formula 10 (1 μM, hereinafter also referred to as 'Refemetinib'). The cells were cultured for 4 days.

Neurospheres were treated with TrypLE and separated into single cells, which were uniformly seeded into a culture dish coated with 15 μg/ml poly-L-ornithine and 10 μg/ml fibronectin. Following culture, the morphology of the cells was observed.

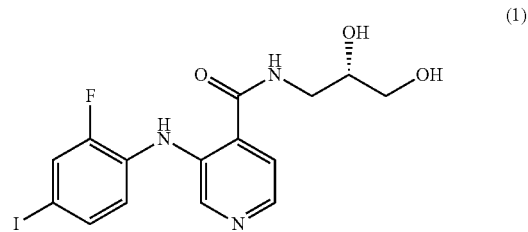 [SMILES: O=C(NC[C@H](O)CO)c1ccncc1Nc1ccc(I)cc1F]

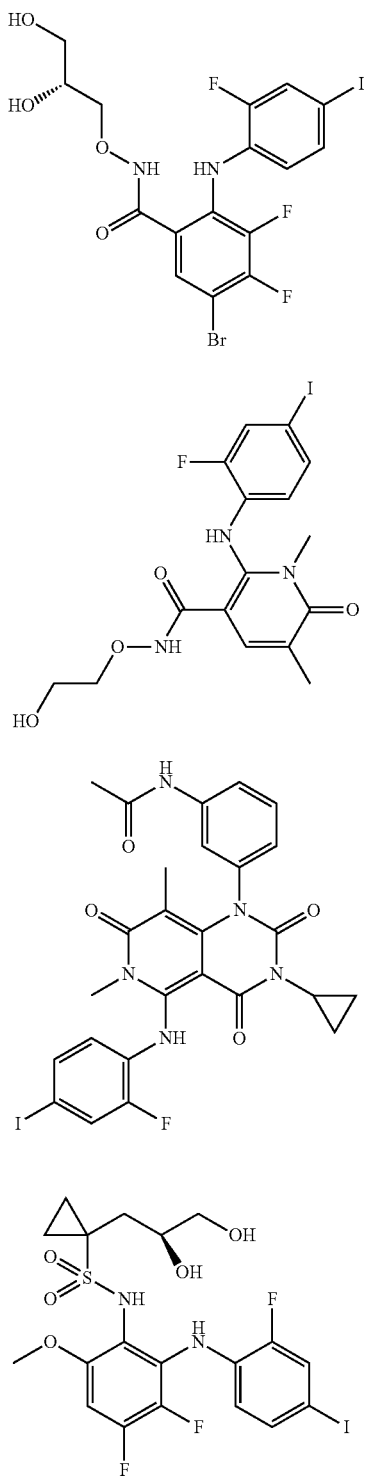

COMPARATIVE EXAMPLE 1

The procedure of Example 2 was repeated except that the composition for differentiation induction including the compound represented by Formula 1 was not added to the culture of neural progenitor cells.

EXPERIMENTAL EXAMPLE 1

In this example, it was confirmed whether the differentiation of neural stem cells into dopaminergic neurons was induced.

To this end, real-time (RT) PCR analysis was performed on neuron-specific markers. On day 4 after in vitro differentiation, mRNA expression was identified. The results are shown in FIGS. 1A an 1B. The numbers in the graph indicate average values of mRNA expression levels relative to the respective controls from real-time PCR analyses in triplicate.

Figure 1B:
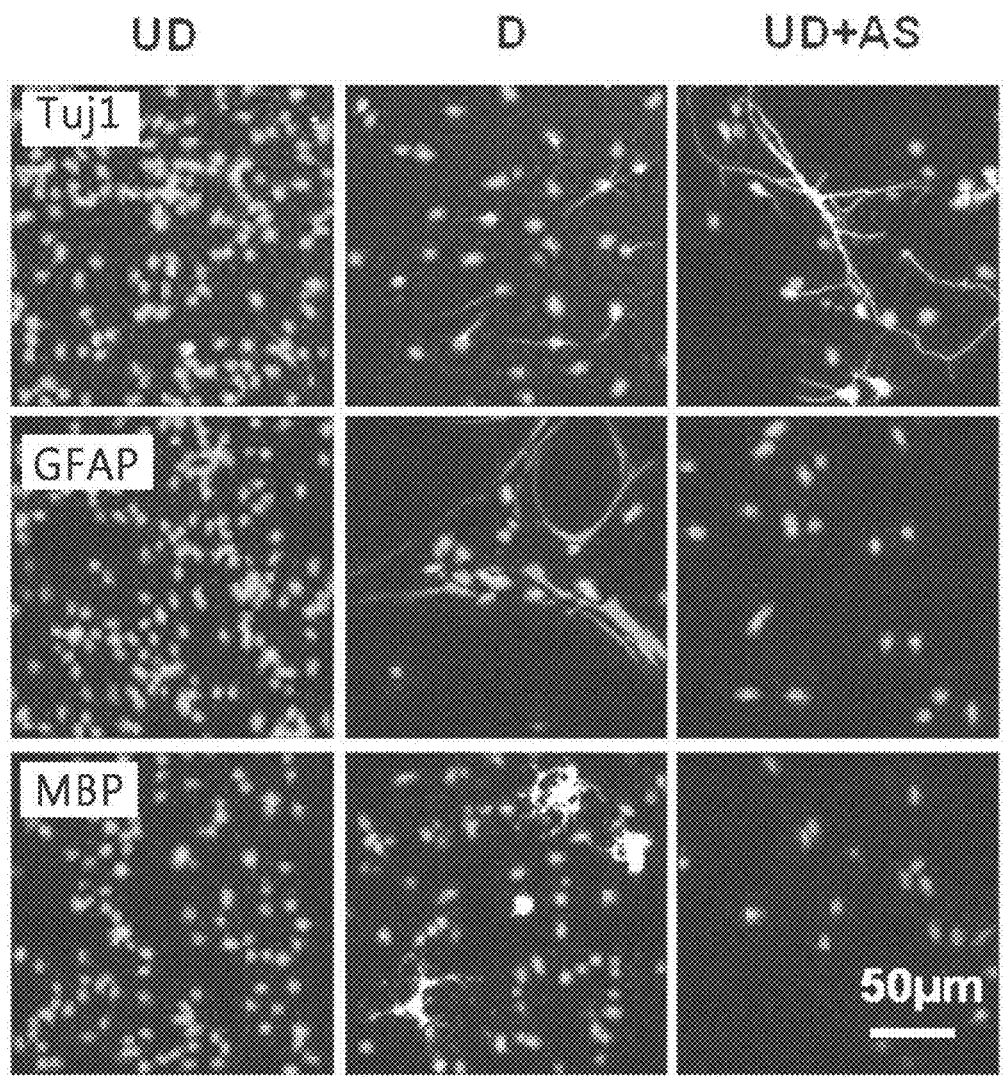
FIG. 1B, the results of immunocytochemical analysis for the neuronal marker (Tuj1) also revealed a considerable increase in the number of neurons differentiated from the AS703026-treated cells (UD+AS) cultured in Example 2 and an increase in the number of clusters of the dopaminergic neurons from which neurites extended outward.

FIGS. 1A and 1B shows the results of RT-PCR analysis and immunocytochemical analysis of neuronal markers for the neural progenitor cells (undifferentiated; UD) cultured in Example 1, the differentiated cells (D) cultured in Comparative Example 1, and the AS703026-treated cells (UD+AS) cultured in Example 2 to determine whether neuronal differentiation factors were expressed, which is an indicative of induction of the differentiation of the cells into neurons.

As shown in FIG. 1A, the expression level of Tuj1, a neuronal differentiation factor, in the AS703026-treated cells (UD+AS) cultured in Example 2 was a maximum of at least 10 times higher than those in the neural progenitor cells (undifferentiated; UD) cultured in Example 1 and the differentiated cells (D) cultured in Comparative Example 1.

The expression levels of GFAP and MBP, differentiation factors of astrocytes and oligodendrocytes as other brain cells, respectively, in the AS703026-treated cells (UD+AS) cultured in Example 2 were lower than that of Tuj1.

As shown in FIG. 1B, the results of immunocytochemical analysis for the neuronal marker (Tuj1) also revealed a considerable increase in the number of dopaminergic neurons differentiated from the AS703026-treated cells (UD+AS) cultured in Example 2 and an increase in the number of clusters of the dopaminergic neurons from which neurites extended outward.

No immune responses to the differentiation factors GFAP and MBP were observed in the AS703026-treated cells (UD+AS) cultured in Example 2.

Taken together, it can be seen that AS703026 induces specific differentiation of neural stem cells into dopaminergic neurons. This suggests that the composition and method for inducing the differentiation of neural stem cells into dopaminergic neurons according to the present invention can be used to treat patients with neurodegenerative diseases, particularly Parkinson's disease.

EXPERIMENTAL EXAMPLE 2

In this example, the cell cycles of the neural progenitor cells (undifferentiated; UD) cultured in Example 1, the differentiated cells (D) cultured in Comparative Example 1, and the AS703026-treated cells (UD+AS) cultured in Example 2 were analyzed and compared to determine whether cytotoxicity of the neural stem cells was caused by treatment with AS703026.

Specifically, the cell cycles were analyzed by the following procedure. First, the cells (Example 1, Example 2, and Comparative Example 1) were washed twice with cold PBS and fixed in cold 70% ethanol for 30 min. The ethanol was removed by centrifugation, the cells were suspended, and the number of the cells was adjusted to $10^6$/ml. The cells were washed twice with PBS, treated with 50 μg/ml propidium iodide (PI) at room temperature in the presence of RNase, and cultured for 30 min.

Finally, the number of the cells was counted using a FACS Calibur flow cytometer (BD Biosciences, USA). Apoptosis was analyzed as follows. The cells were washed twice with cold PBS, treated with propidium iodide (PI) and Annexin V FITC at room temperature, and cultured for 15 min. PI and FITC fluorescence intensities were measured using a FACS flow cytometer. Data were analyzed with the Cell-quest FACS analysis software (BD Biosciences). The results are shown in FIGS. 2A, 2B, 2C, 3A, 3B and 3C.

FIGS. 2A, 2B, 2C, 3A, 3B and 3C show the results of flow cytometry for the neural progenitor cells (undifferentiated; UD) cultured in Example 1, the differentiated cells (D) cultured in Comparative Example 1, and the AS703026-treated cells (UD+AS) cultured in Example 2 to identify the cycles of the cells. Specifically, FIGS. 2A, 2B and 2C are histograms showing the results of flow cytometry for the cells stained with PI. FIGS. 3A, 3B and 3C are scatter plot diagrams showing the results of flow cytometry for the cells stains with annexin-V/PI.

The differentiation of neural stem cells is induced with cell cycle arrest and causes cytotoxicity by treatment with the low molecular weight compound, which were identified by measuring the cell cycle of the neural stem cells.

As shown in FIG. 2C, the cell cycle of the AS703026-treated cells (UD+AS) cultured in Example 2 was arrested in the G0/G1 phase.

The cell cycles were analyzed to determine whether cell cycle arrest is associated with cytotoxicity. The results indicate that AS703026 does not induce apoptosis.

In conclusion, the composition for differentiation induction including AS703026 and the method for differentiation induction according to the present invention induce cell cycle arrest and differentiation into dopaminergic neurons without cytotoxicity.

EXPERIMENTAL EXAMPLE 3

In this example, it was confirmed whether dopaminergic neurons were differentiated from neural stem cells. To this end, immunoblot analysis and immunocytochemical analysis were performed on the neural progenitor cells (undifferentiated; UD) cultured in Example 1, the differentiated cells (D) cultured in Comparative Example 1, and the AS703026-treated cells (UD+AS) cultured in Example 2 and the results were compared. The results are shown in FIGS. 4 and 5.

The immunoblot analysis was performed by the following procedure. First, the cells were washed with ice-cold phosphate-buffered saline (PBS) and lysed with 1×RIPA buffer (10 mM HEPES, 1.5 mM $MgCl_2$, 10 mM KCl, 0.01 M DTT, protease inhibitors, pH 7.9). The cell homogenate was heated at 100° C. for 10 min and subjected to 10-12% SDS-polyacrylamide gel electrophoresis. Proteins were electrophoretically transferred to a nitrocellulose membrane and blocked with 5% non-fat dry milk in TBS-Tween 20 (0.1%, v/v) for 1 h. Western blotting was performed using anti-Tuj1, anti-GFAP or anti-MBP antibodies and successively horseradish peroxidase-conjugated anti-rabbit or anti-mouse IgG secondary antibodies. The protein bands were visualized using enhanced chemiluminescence (ECL, lab made) and detected with LAS-3000 (FUJIFILM, Tokyo, Japan).

The immunocytochemical analysis was performed by the following procedure. First, the cells were fixed in 4% para-formaldehyde at room temperature for 10 min, washed with PBS, and incubated with 0.2% Triton X-100 at room temperature for 15 min. After blocking with 10% BSA at room temperature for 1 h, the cells were incubated with anti-Tuj1 (Covance, Princeton, N.J.), anti-GFAP (Biogenex, San Ramon, Calif.), anti-MBP (Abcam), anti-Ki67 (Abcam), anti-p-ERK1/2 or anti-TH antibodies at 4° C. overnight, and cultured using Alexa Fluor 488- or Alexa Fluor 555-conjugated IgG secondary antibodies (Molecular Probes, Eugene, Oreg.) at room temperature for 1 h. Subsequently, the cells were cultured with 1 μg/ml 4',6-diamidino-2-phenylindole (DAPI) for 5 min, the inlet was sealed with a coverslip, and the cells were observed using a confocal microscope.

Figure 4:
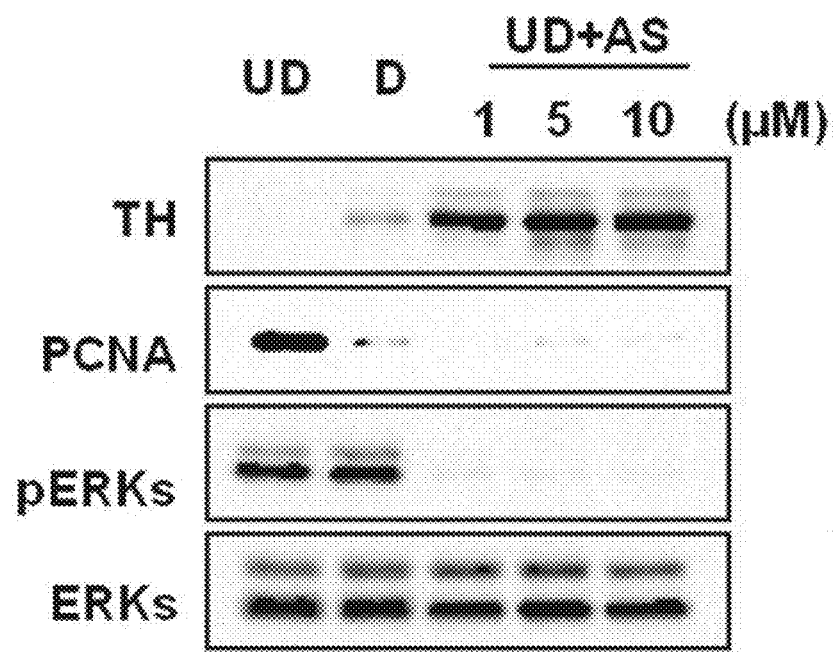
FIG. 4 shows the results of immunoblot analysis for neural progenitor cells (undifferentiated; UD) cultured in Example 1, differentiated cells (D) cultured in Comparative Example 1, and AS703026-treated cells (UD+AS) cultured in Example 2 to determine whether dopaminergic neurons were differentiated from the neural stem cells.
Figure 5:
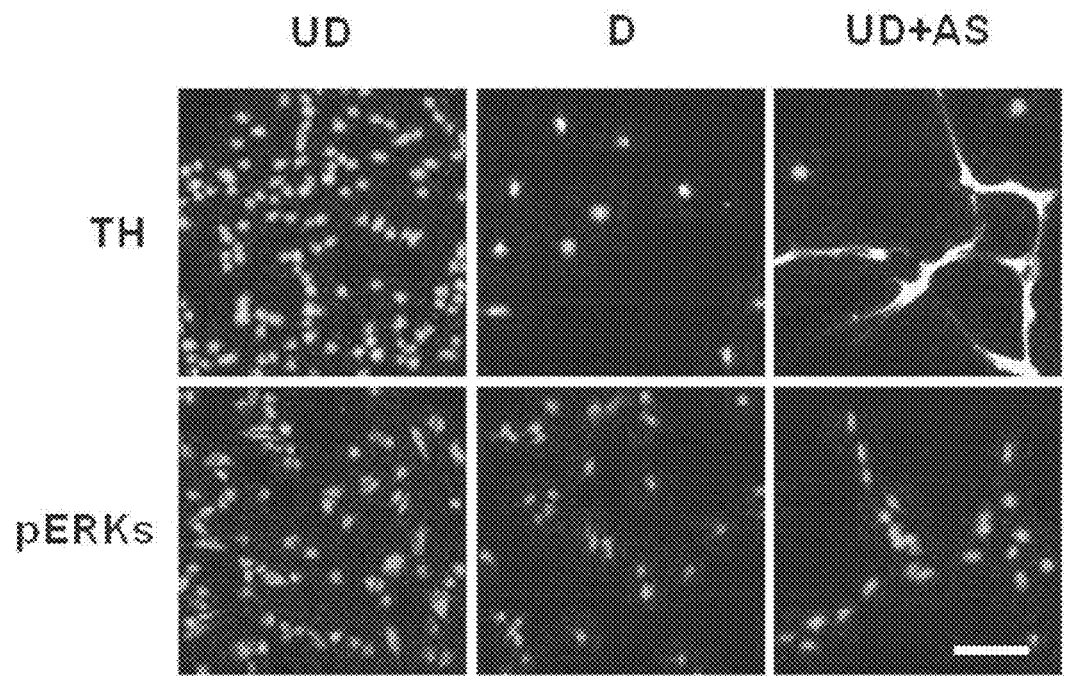
FIG. 5 shows the results of immunocytochemical analysis for neural progenitor cells (undifferentiated; UD) cultured in Example 1, differentiated cells (D) cultured in Comparative Example 1, and AS703026-treated cells (UD+AS) cultured in Example 2 to determine whether dopaminergic neurons were differentiated from the neural stem cells.

FIGS. 4 and 5 show the results of immunoblot analysis (FIG. 4) and immunocytochemical analysis (FIG. 5) for the neural progenitor cells (undifferentiated; UD) cultured in Example 1, the differentiated cells (D) cultured in Comparative Example 1, and the AS703026-treated cells (UD+AS) cultured in Example 2 to determine whether dopaminergic neurons were differentiated from the neural stem cells.

As shown in FIGS. 4 and 5, tyrosine hydroxylase (TH), a marker of dopaminergic neurons, was expressed only in the AS703026-treated cells (UD+AS) cultured in Example 2.

That is, the treatment of the culture of the neural stem cells with the composition for differentiation induction including AS703026 effectively induced the differentiation of the neural stem cells into dopaminergic neurons while preventing the differentiation of the neural stem cells into other cells.

The procedure of Example 2 was repeated except that the cells were treated with AS703026 at concentrations of 1 μM and 5 μM. The AS703026-treated cells were cultured in the same manner as in Example 2. The expression patterns of the marker of dopaminergic neurons (TH) in the cultured cells (UD+AS, 1) (UD+AS, 5) were similar to that in the cells (UD+AS) cultured in Example 2.

These results indicate that the differentiation of the neural stem cells into dopaminergic neurons can be induced when the concentration of AS703026 in the composition for differentiation induction is from 0.5 to 20 μM, based on the culture of the neural stem cells. The AS703026 concentration is more preferably from 1 to 10 μM.

EXPERIMENTAL EXAMPLE 4

In vivo Implantation

In this example, the therapeutic effects of the composition for differentiation induction including AS703026 on dopaminergic neurons were observed. Specifically, after the composition for differentiation induction including AS703026 was administered intraperitoneally to pregnant mouse models at 10.5 days of gestation daily for 4 consecutive days, the expression levels of the markers in the ventral midbrains, where dopaminergic neurons were most abundantly distributed, were analyzed. The results are shown in FIGS. 6 and 7.

After the same amount of distilled water (D.W) as control was administered intraperitoneally to pregnant mouse models at 10.5 days of gestation daily for 4 consecutive days, the expression levels of the markers in the ventral midbrains, where dopaminergic neurons were most abundantly distributed, were analyzed. The control is marked as "Vehicle" in FIGS. 6 and 7.

As shown in FIGS. 6 and 7, the expression levels of Tuj1 as the marker of neurons and TH as the marker of dopaminergic neurons in the brains of the embryos sacrificed after treatment with the composition for differentiation induction including AS703026 were significantly higher than those in the control, as revealed in the above in vitro results.

Proteins and mRNAs isolated from the brains of the sacrificed embryos were analyzed by RT-PCR. The results are shown in FIG. 7. In the embryos sacrificed after treatment with the composition for differentiation induction including AS703026, increased differentiation into dopaminergic neurons was observed. No immune responses to GFAP and MBP, differentiation factors of astrocytes and oligodendrocytes as other brain cells, respectively, were observed. From these results, it can be seen that the composition for differentiation induction including AS703026 does not induce the differentiation of neural stem cells into other types of cells.

EXPERIMENTAL EXAMPLE 5

In this example, it was confirmed whether dopaminergic neurons were differentiated from neural stem cells. To this end, RT-PCR analysis, which is an indicative of induction of the differentiation of the cells into neurons and expression of marker of dopaminergic neurons, were performed on the neural progenitor cells (undifferentiated; UD) cultured in Example 1, the differentiated cells (D) cultured in Comparative Example 1, and the AS703026, PD318088, AZD8330, Trametinib or Refametinib-treated cells cultured by the method described in Example 2, and the results were compared. The results are shown in FIGS. 8A, 8B and 8C.

Figure 8A:
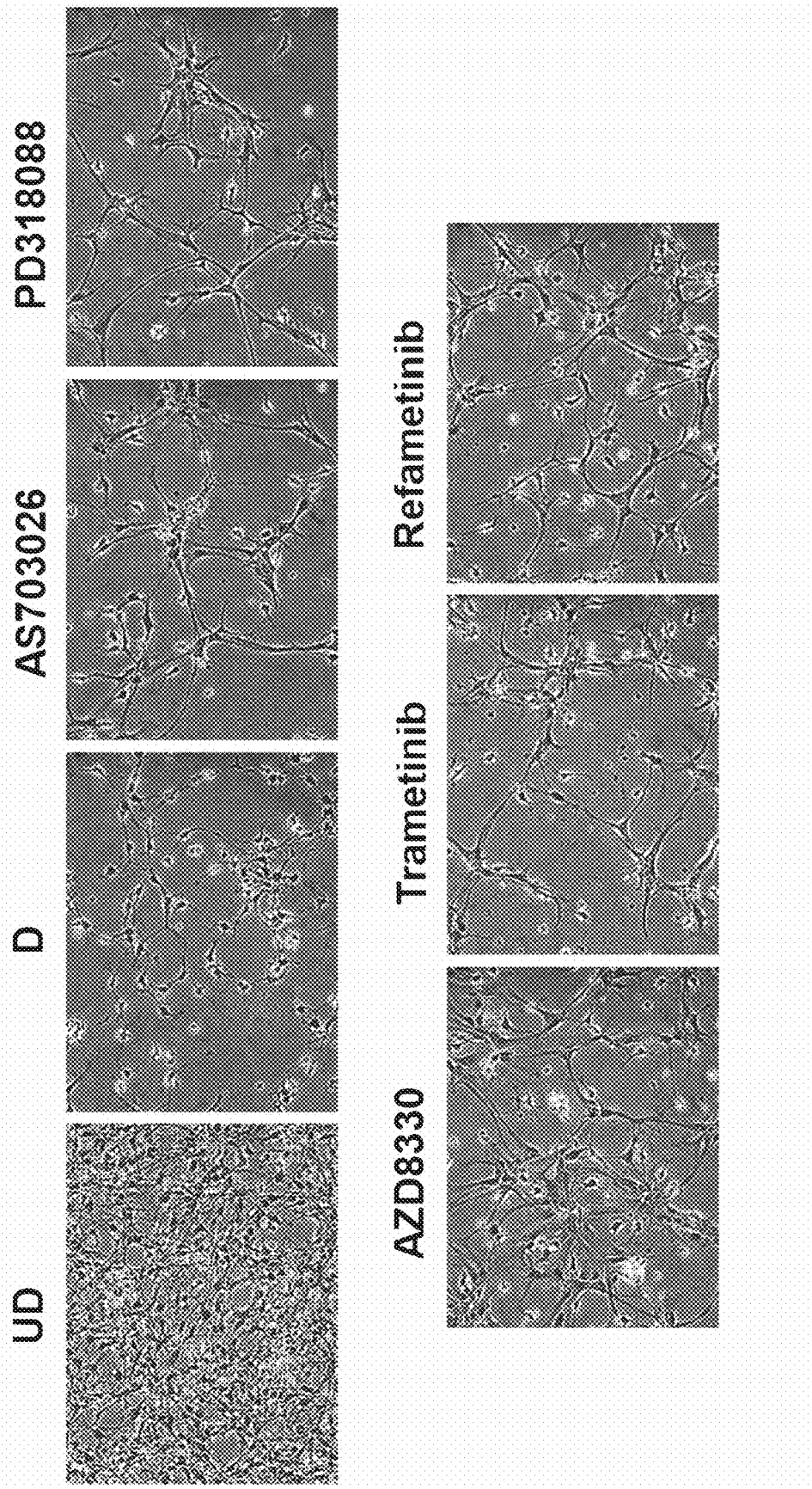
FIG. 8A, the results of morphological analysis also revealed a considerable change to neuronal differentiated morphology from the AS703026, PD318088, AZD8330, Trametinib or Refametinib-treated cells cultured in the method by described in Example 2 and an increase in the number of clusters of the dopaminergic neurons from which neurites extended outward.
Figure 8B:
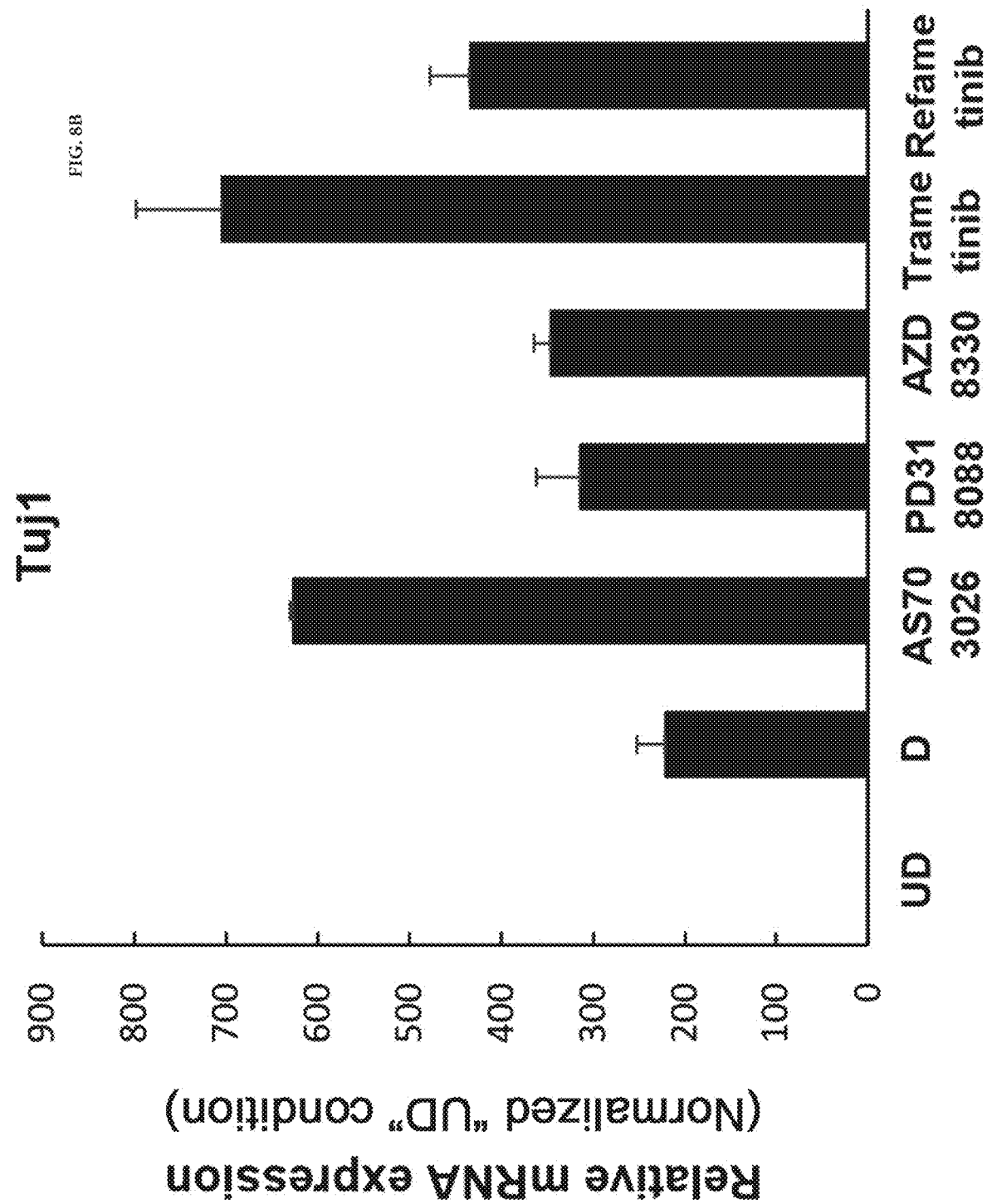
FIG. 8B shows the mRNA expression level of Tuj1, a neuronal differentiation factor, in the AS703026, PD318088, AZD8330, Trametinib or Refametinib-treated cells cultured in the method by described in Example 2 was increased 315 to 705 times as much as in the neural progenitor cells (undifferentiated; UD) cultured in Example 1.
Figure 8C:
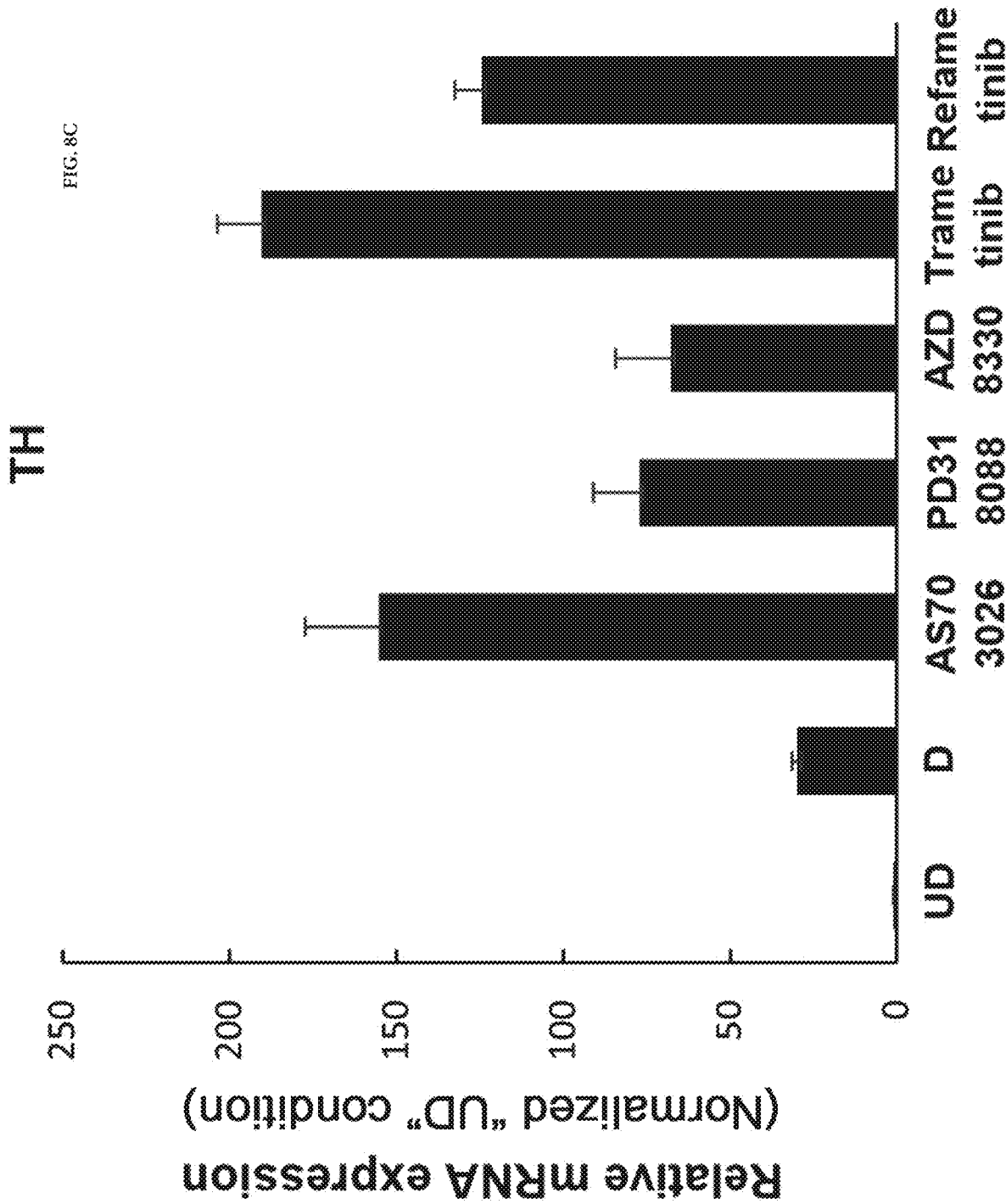
FIG. 8C shows the mRNA expression level of tyrosine hydroxylase (TH), a marker of dopaminergic neurons, in the AS703026, PD318088, AZD8330, Trametinib or Refametinib-treated cells cultured in the method by described in Example 2 was increased 315 to 705 times as much as in the neural progenitor cells (undifferentiated; UD) cultured in Example 1.

As shown in FIG. 8A, the neuron-like morphological changes were shown in the AS703026, PD318088, AZD8330, Trametinib or Refametinib-treated cells cultured by the method described in Example 2. In addition, FIG. 8B, Tuj1, a marker of neurons, was expressed only in the AS703026, PD318088, AZD8330, Trametinib or Refametinib-treated cells cultured by the method described in Example 2. And as shown in FIG. 8C, tyrosine hydroxylase (TH), a marker of dopaminergic neurons, was expressed only in the AS703026, PD318088, AZD8330, Trametinib or Refametinib-treated cells cultured by the method described in Example 2.

And an induction of the differentiation of the cells into neurons and the differentiation of the neural stem cells into dopaminergic neurons is confirmed in all group of the MEK 1/2 inhibitors treated cell, but not in the neural progenitor cells (undifferentiated; UD).

That is, the treatment of the culture of the neural stem cells with the composition for differentiation induction including AS703026 and the MEK 1/2 inhibitors which are PD318088, AZD8330, Trametinib or Refametinib, effectively induced the differentiation of the neural stem cells into dopaminergic neurons while preventing the differentiation of the neural stem cells into other cells.

These results indicate that the differentiation of the neural stem cells into dopaminergic neurons can be induced when the concentration of AS703026 and the MEK 1/2 inhibitors which are PD318088, AZD8330, Trametinib or Refametinib, in the composition for differentiation induction is from 0.5 to 20 μM, based on the culture of the neural stem cells. The AS703026 concentration is more preferably from 1 to 10 μM.

The invention claimed is:

1. A method for treatment of a motor disorder of Parkinson's disease, wherein the disease is caused by congenital or acquired damage to or loss of dopaminergic neurons, comprising:
    administering a composition comprising a MEK 1/2 inhibitor as a sole effective component,
    wherein the MEK 1/2 inhibitor is a compound according to formula (1)

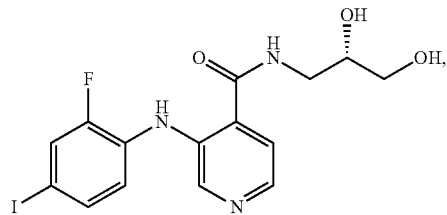 [SMILES: O=C(NC[C@H](O)CO)c1ccncc1Nc1ccc(I)cc1F]

wherein the composition differentiates neural stem cells of a patient with the motor disorder of Parkinson's disease into dopaminergic neuron.

2. The method according to claim 1, wherein the MEK 1/2 inhibitor is present at a concentration of 0.1 to 20 μM.

3. The method according to claim 1, wherein the MEK 1/2 inhibitor is present at a concentration of 1 to 10 μM.

4. The method according to claim 1, wherein the composition inhibits growth of cancer cells from neural stem cells.

5. The method according to claim 1, further comprising inoculating a pre-composition comprising neural stem cells with the MEK 1/2 inhibitor to provide the composition.

6. The method according to claim 5, wherein the neural stem cells are allowed to differentiate for 1 to 7 days.

* * * * *